US010342949B2

(12) United States Patent
Lin

(10) Patent No.: US 10,342,949 B2
(45) Date of Patent: Jul. 9, 2019

(54) GAS GENERATOR FOR HEALTH USE HAVING SECURITY SYSTEM

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 697 days.

(21) Appl. No.: 14/508,656

(22) Filed: Oct. 7, 2014

(65) Prior Publication Data

US 2015/0101601 A1   Apr. 16, 2015

(30) Foreign Application Priority Data

Oct. 10, 2013  (CN) ..................... 2013 2 0624031 U

(51) Int. Cl.
| A61M 16/12 | (2006.01) |
| A61M 16/10 | (2006.01) |
| A61M 16/14 | (2006.01) |
| C25B 1/04 | (2006.01) |
| C25B 15/02 | (2006.01) |
| C25B 15/08 | (2006.01) |

(Continued)

(52) U.S. Cl.
CPC ............ *A61M 16/12* (2013.01); *A61M 16/10* (2013.01); *A61M 16/14* (2013.01); *C25B 1/04* (2013.01); *C25B 15/02* (2013.01); *C25B 15/08* (2013.01); *A61M 11/005* (2013.01); *A61M 15/0085* (2013.01); *A61M 15/08* (2013.01); *A61M 16/16* (2013.01); *A61M 16/209* (2014.02); *A61M 2016/0027* (2013.01); *A61M 2202/0208* (2013.01); *A61M 2205/15* (2013.01); *A61M 2205/17* (2013.01); *A61M 2205/18* (2013.01); *A61M 2205/3331* (2013.01); *A61M 2205/3368* (2013.01); *A61M 2205/3389* (2013.01); *A61M 2205/3606* (2013.01); *A61M 2205/502* (2013.01); *A61M 2205/82* (2013.01); *A61M 2205/84* (2013.01); *Y02E 60/366* (2013.01)

(58) Field of Classification Search
CPC .. A61M 16/12; A61M 16/16; A61M 2205/82; A61M 2205/502; A61M 11/005; C25B 15/02
See application file for complete search history.

(56) References Cited

U.S. PATENT DOCUMENTS 3,828,773 A * 8/1974 Buch ................. A61M 15/0085
128/200.16
3,874,379 A * 4/1975 Enfield .................. A61M 11/06
128/200.18

(Continued)

*Primary Examiner* — Timothy A Stanis
(74) *Attorney, Agent, or Firm* — Foster Pepper PLLC

(57) ABSTRACT

The present invention provides a gas generator for health use having a security system, comprising: an electrolysis tank for containing electrolyzed water, wherein the electrolysis tank further comprises a power supply for electrolyzing the electrolyzed water to generating a gas mixture including hydrogen and oxygen; and a water bucket, coupled to the electrolysis tank. The security system comprises a sensor, electrically connected to the power supply, used to control the switch of the power supply, wherein the sensor is selected from a group consisting of a water level sensor configured in the water bucket, a gas leakage sensor configured in the gas generator for health use, a temperature sensor configured in the water bucket, a temperature sensor configured in the electrolysis tank, a temperature sensor configured in the power supply, and a combination thereof.

9 Claims, 4 Drawing Sheets

(51) Int. Cl.
   *A61M 11/00*    (2006.01)
   *A61M 15/00*    (2006.01)
   *A61M 15/08*    (2006.01)
   *A61M 16/16*    (2006.01)
   *A61M 16/00*    (2006.01)
   *A61M 16/20*    (2006.01)

(56) References Cited

U.S. PATENT DOCUMENTS

| | | | | |
|---|---|---|---|---|
| 4,413,622 A * | 11/1983 | Austin | .................... | A62B 7/00 128/202.13 |
| 5,082,544 A * | 1/1992 | Willey | .................... | C25B 15/00 204/270 |
| 5,170,637 A * | 12/1992 | Shyu | .................... | F24F 3/12 204/242 |
| 5,259,370 A * | 11/1993 | Howe | .................... | A61M 16/16 128/200.14 |
| 5,690,797 A * | 11/1997 | Harada | .................... | C25B 1/12 204/228.5 |
| 6,495,025 B2 * | 12/2002 | Velev | .................... | C25B 1/04 204/263 |
| 7,100,603 B1 * | 9/2006 | Krasberg | .................... | A61M 16/0627 128/200.24 |
| 7,504,015 B2 * | 3/2009 | Hecker | .................... | B01D 53/326 204/263 |
| 7,682,428 B2 * | 3/2010 | Nawata | .................... | A61M 16/10 96/113 |
| 8,123,916 B2 * | 2/2012 | Blenkiron | .................... | C25B 15/00 204/242 |
| 2003/0051998 A1 * | 3/2003 | Lin | .................... | C25B 1/04 204/274 |
| 2004/0038096 A1 * | 2/2004 | Chou | .................... | C25B 15/02 429/413 |
| 2005/0178381 A1 * | 8/2005 | Daugherty | .................... | A61M 16/08 128/203.12 |
| 2005/0181244 A1 * | 8/2005 | Porter | .................... | F17C 7/00 429/425 |
| 2010/0155233 A1 * | 6/2010 | Hwang | .................... | C25B 1/04 204/228.6 |
| 2011/0247620 A1 * | 10/2011 | Armstrong | .................... | B01D 53/047 128/204.23 |
| 2012/0017904 A1 * | 1/2012 | Ratto | .................... | A61M 16/0666 128/203.26 |
| 2013/0206586 A1 * | 8/2013 | Lin | .................... | C25B 15/02 204/228.2 |

* cited by examiner

GAS GENERATOR FOR HEALTH USE HAVING SECURITY SYSTEM

PRIORITY CLAIM

This application claims the benefit of the filing date of China Patent Application No. 201320624031.5, filed Oct. 10, 2014, entitled "A GAS GENERATOR FOR HEALTH USE HAVING SECURITY SYSTEM," and the contents of which are hereby incorporated by reference in their entirety.

FIELD OF THE INVENTION

The present invention relates to a gas generator for health use, and more particularly, to a gas generator for health use having a security system.

BACKGROUND

People always pay great attention on life. Many developments of medical technologies are used to treat diseases to prolong human life. Most of the treatments in the past are passive, which means only treating the disease when the disease occurs, such as operating, medicating, radiotherapy, convalescing for chronic disease, rehabilitation, corrective therapy, or even medical treatment for cancer. But in recent years, many researches of medical experts are gradually forward to preventive medical method, such as research of health food, screening and preventing for inherited disease, which actively prevents the diseases may occur in the future. Besides, for prolonging human life, many technologies of anti-aging and anti-oxidation including skin care products and anti-oxidation food/medicine are gradually developed and have been used by people generally.

In recent years, people have been noticing the benefits of aromatherapy. Aromatherapy is a natural way to make people feel relaxed and become healthy. Essential oils are extracted from aromatic plants to act as a medium which is then exposed to someone by massaging, bathing, perfuming and so on. This method has existed since the ancient times of Egypt and is now gaining a lot of attention in Europe. In the prior art, people found that the plant's essential oils can reach into the deep tissue layers of skin, that is then absorbed by blood vessels and reaches organs that can only be treated through blood circulation.

Therefore, the present invention provides a gas generator for health use having security system. The gas generator can generate health gas for health care that makes people feel relaxed and is also suitable for medical treatment. And through the monitoring of the security system, the present invention can prevent gas leakage, overheating, or hydrogen explosion of the gas generator for enhancing using security.

SUMMARY OF THE INVENTION

A viewpoint of the present invention is to provide a gas generator for health use having a security system. The present invention can monitor water level and/or temperature of the water bucket for controlling the filling water mechanism and the electrolysis tank and then enhancing the security of the gas generator.

Another viewpoint of the present invention is to provide a gas generator for health use having a security system. The present invention can monitor temperature of the electrolysis tank for controlling the electrolysis tank and then enhancing the security of the gas generator.

Another viewpoint of the present invention is to provide a gas generator for health use having a security system. The present invention can monitor temperature of the power supply for controlling the electrolysis tank and then enhancing the security of the gas generator.

Another viewpoint of the present invention is to provide a gas generator for health use having a security system. An emergency button is set for user to cut off the power supply of the gas generator when there is an emergency situation to enhance the security of the gas generator.

According to one embodiment of the present invention, the present invention provides a security system for a gas generator for health use, wherein the gas generator comprises gas generator and a water bucket. The electrolysis tank is used for containing first electrolyzed water. The electrolysis tank further comprises a power supply for electrolyzing the first electrolyzed water to generate a gas mixture including hydrogen and oxygen. The water bucket is used for containing second electrolyzed water and coupled to the electrolysis tank, wherein the electrolysis tank is coupled to the water bucket through a first pipe for outputting the gas mixture including hydrogen and oxygen through the first pipe to a gas exit of the water bucket, and the water bucket is coupled to the electrolysis tank through a second pipe for outputting the second electrolyzed water through the second pipe to the electrolysis tank. The security system comprises a first temperature sensor, configured in the electrolysis tank and electrically connected to the power supply. When the first temperature sensor senses the temperature of the electrolysis tank is higher than a preset value, the first temperature sensor causes the power supply to be cut off.

According to another embodiment of the present invention, the present invention provides a security system further comprising a gas leakage sensor, configured in the gas generator and electrically connected to the power supply. When the gas leakage sensor senses an abnormal gas leakage from the gas generator, the gas leakage sensor causes the power supply to be cut off. The security system further comprises a water level sensor, configured in the water bucket and electrically connected to the power supply. When the water level sensor senses the water level of the water bucket is lower than a preset value, the water level sensor causes the power supply to be cut off. When the water bucket is filling water, if the water level sensor senses the water level of the water bucket is higher than a preset value, the process of filling water is stopped. The security system further comprises a second temperature sensor, configured in the water bucket and electrically connected to the power supply. When the second temperature sensor senses the temperature of the water bucket is higher than a preset value, the second temperature sensor causes the power supply to be cut off. The security system further comprises a third temperature sensor, configured in the power supply and electrically connected to the power supply. When the third temperature sensor senses the temperature of the power supply is higher than a preset value, the third temperature sensor causes the power supply to be cut off.

According to another embodiment of the present invention, the present invention provides a security system further comprising an emergency button, coupled to the power supply. The emergency button is used to cut off the power supply when the emergency button is pushed by a user. The security system further comprises a displayer, configured in the gas generator to display an abnormal condition of the gas generator.

According to another embodiment of the present invention, the present invention provides a security system for a gas generator for health use, wherein the gas generator comprises: an electrolysis tank for containing first electrolyzed water, wherein the electrolysis tank further comprises a power supply for electrolyzing the first electrolyzed water to generating a gas mixture including hydrogen and oxygen; and a water bucket, coupled to the electrolysis tank. The security system comprises a sensor, electrically connected to the power supply, used to control the switch of the power supply, wherein the sensor is selected from a group consisting of a water level sensor configured in the water bucket, a gas leakage sensor configured in the gas generator for health use, a temperature sensor configured in the water bucket, a temperature sensor configured in the electrolysis tank, a temperature sensor configured in the power supply, and a combination thereof.

According to some embodiments of the present invention, the security system further comprises an alarm device, coupled to the sensor for cutting off the power supply for actuating the alarm device when the sensor senses an abnormal condition.

According to the security system provided by the present invention, the temperature of relative device can be monitored by the temperature sensor configured in the electrolysis tank, water bucket, and power supply, which can prevent air blast or short circuit due to an over high temperature for enhancing the security of the gas generator. The water level sensor configured in the water bucket can monitor the water level of the water bucket for controlling the filling water mechanism and the stored volume of the gas mixture including hydrogen and oxygen in the water bucket, which can prevent hydrogen explosion due to an over high pressure or too much stored volume of the gas mixture in the water bucket for assuring the security of the gas generator.

The advantages and spirits of the invention may be understood by the following recitations together with the appended drawings.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Studies have found that there is an instable oxygen species (O+), also known as free radicals, in the human body. The free radicals are usually generated due to diseases, diet, environment and one's life style, and the free radicals in the human body can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are clinical experiments showing that, for patients who need to inhale a high concentration of oxygen for a long time, the lung damage from the high concentration of oxygen can be ameliorated by inhaling hydrogen. According to the statement mentioned above, gas including hydrogen can be believed in a health gas, which can be generated by electrolyzing water.

Figure 1:
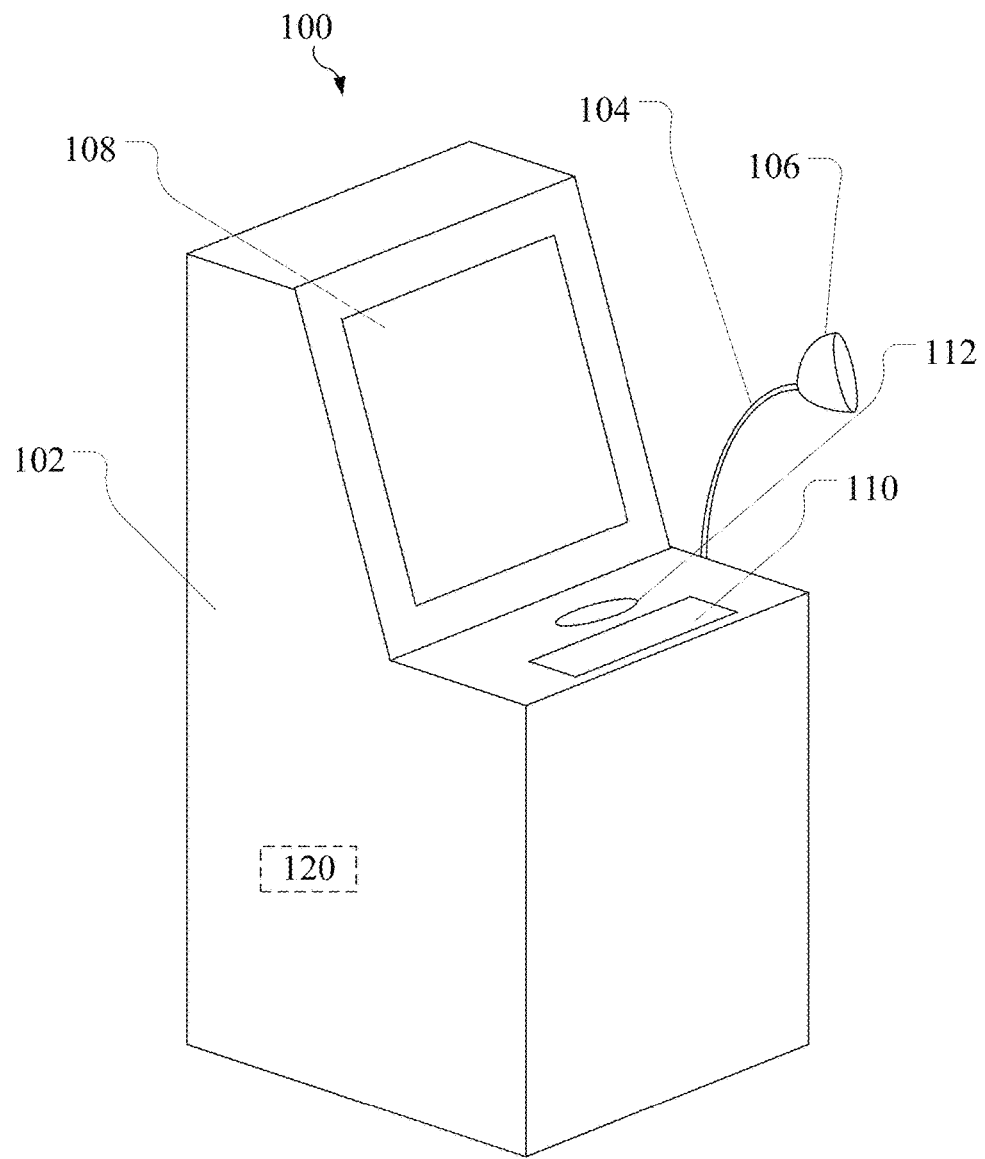
FIG. 1 shows the gas generator for health use in an embodiment of the present invention.
Figure 2:
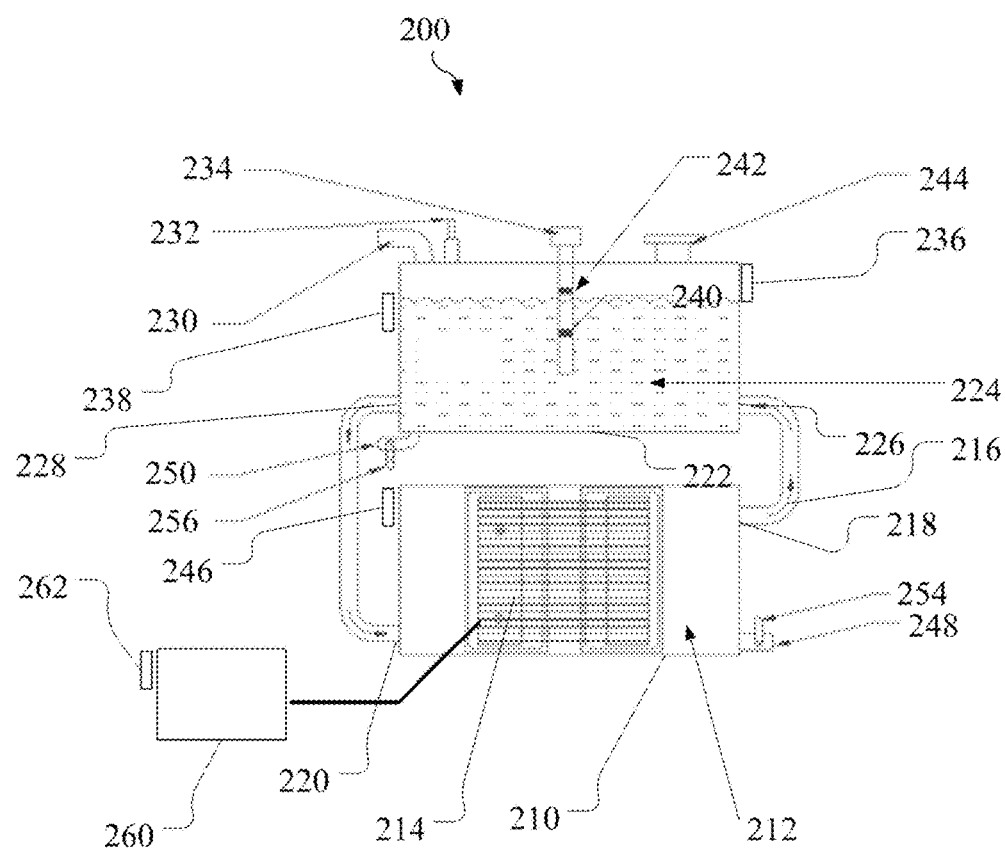
FIG. 2 shows the partial components of the gas generator for health use in an embodiment of the present invention.

Please refer to FIG. 1. FIG. 1 shows the gas generator for health use in an embodiment of the present invention. According to some embodiment of the present invention, the gas generator 100 comprises a main body 102. The main body 102 comprises relative device for generating health gas including hydrogen and oxygen and mixing the gas mixture including hydrogen and oxygen with a volatile essential oil and an atomized medicinal liquid. The relative detail will be explained later. The gas generator 100 further comprises a mask 106, connected to the relative device for generating health gas comprised in the main body 102 through a pipe 104 to provide health gas including hydrogen and oxygen for user to breathe. The gas generator 100 further comprises a display device 108, such as a display panel including liquid crystal display panel, light emitting diode display panel or touch screen. The display device 108 is used to display relative information of the gas generator 100, wherein the relative information comprises: the using state of the gas mixture including hydrogen and oxygen, atomized medicinal liquid, or volatile essential oil, such as flow rate, temperature, or pressure; or the using state of relative devices, such as the temperature, water level, or pressure of the electrolysis tank or the water bucket; or some relative alarm messages, for example, the system has gas leakage, the gas pressure of the gas mixture including hydrogen and oxygen is too high, the temperature of devices is too high, or the water level of the electrolysis tank or the water bucket is abnormal. In some embodiments, the display device 108 can further display relative information of the user, wherein the relative information includes account, used times, used volume, or suggested setting. In another embodiment, the gas generator of the present invention further comprises network system, used to connect the using state or relative data of the user to the account database for providing data exchanging function, such as relative verification or updating function. And all the relative information can be displayed through the display device 108. In another embodiment, the gas generator of the present invention further comprises video system, used to play video or music for user when using. And the relative information can also be displayed through the display device 108. The gas generator 100 further comprises an input device 110, such as keyboard or touch panel, for the user to input relative messages, including account, setting, or function selecting. The input device 110 also can adjust the output rate of the atomized medicinal liquid, volatile essential oil, or the gas mixture including hydrogen and oxygen, Please refer to FIG. 2. FIG. 2 shows the partial components of the gas generator for health use in an embodiment of the present invention. According to some embodiments of the present invention, the main body 102 in FIG. 1 comprises a hydrogen and oxygen generator 200, wherein the generator comprises an electrolysis tank 210 for containing electrolyzed water 212. The main component of the electrolyzed water 212 is pure water or water. Some electrolytes can be added when needing, such as Sodium hydroxide, Calcium carbonate, or Sodium chloride solution. In this embodiment, the electrolysis tank 210 is a plate form electrolysis tank, comprising many plate form electrodes 214 electrically connected to the power supply 260. The electrolyzed water 212 can be electrolyzed through powering up the power supply 260 for generating gas mixture including hydrogen and oxygen 216. In another embodiment, the electrolysis tank 210 also can be a double crest electrolysis tank. The electrode is formed by a double crest barrel. The double crest barrel has an outer barrel, a middle barrel, and an inner barrel. The middle barrel is a main anode electrically connected to the power supply, so the material is conductive metal, such as stainless steel or other metal coated with platinum. Outer barrel, the middle barrel and the inner barrel are hollow cylinder structures. The inner surface of the outer barrel comprises many teeth structures (for example, the teeth structure is not less than forty teeth). The inner and outer surfaces of the middle barrel also comprise many teeth structures (for example, the teeth structure is not less than forty teeth). And the outer surface of the inner barrel also comprises many teeth structures (for example, the teeth structure is not less than forty teeth). Therefore, the electrolyzing area of the electrodes can be increased. In some embodiments, the polarity of the plate form electrodes of the plate form electrolysis tank and the polarity of the double crest barrel of the double crest electrolysis tank are unchangeable. And in other embodiments, the polarity of the electrodes is changeable for prolonging the using life of the electrolysis tank. However, the electrode form of the electrolysis tank 210 is not limited to the form provided by this embodiment of the present invention. Because the gas mixture including hydrogen and oxygen 216 will be acquired on the top of the electrolysis tank 210, a first gas exit 218 is set on the top of the electrolysis tank 210 of the present invention, which is used to output the generated gas mixture including hydrogen and oxygen 216. The electrolyzed water 212 in the electrolysis tank 210 is consumed due to electrolyzing process, so the electrolysis tank 210 further comprises a first filling water entrance 220, used to fill pure water, and can be set on the bottom of the electrolysis tank 210 as shown in the FIG. 2. The input device 110 of the gas generator 100 can be used for adjusting the output voltage or output current of the power supply 260 by user, which further controls the output rate of the gas mixture including hydrogen and oxygen 216. For example, the input device 100 controls the output rate of the gas mixture including hydrogen and oxygen between 0.1 L/min and 2 L/min, wherein the better output rate is 0.25 L/min.

The water bucket 222 for containing pure water 224 (also can contain electrolyzed water) is used to fill up the electrolysis tank 210. A gas entrance 226 is configured in the water bucket 222, coupled to the first gas exit 218 of the electrolysis tank 210 through a pipe. The gas entrance 226 can direct the gas mixture including hydrogen and oxygen 216 generated from the electrolysis tank 210 into the pure water 224 in the water bucket 222. Only a little gas mixture including hydrogen and oxygen 216 dissolves in the pure water 224. Most gas mixture including hydrogen and oxygen 216 will emerge from the pure water 224 to the top of the water bucket 222. During the process of the gas mixture including hydrogen and oxygen 216 emerging from the pure water 224, most heat energy will be absorbed by the pure water 224 for cooling the temperature of the gas mixture including hydrogen and oxygen 216 due to the high specific heat of the pure water 224, which allows the temperature of the gas mixture including hydrogen and oxygen 216 to be closer to the temperature of the pure water 224, such as room temperature (25° C.). Therefore, the probability of hydrogen explosion caused by the gas mixture including hydrogen and oxygen 216 can be decreased, which enhances the security of the system. In an embodiment, the gas entrance 226 is configured on the outer surface of the bottom half of the water bucket 222 as shown in FIG. 2. Generally, the location of the gas entrance 226 has to be lower than the water level of the water bucket 222 when normal using. A little needless electrolyzing gas of the gas mixture including hydrogen and oxygen 216 can also dissolve in the pure water, such as chlorine gas, which has the effect of filtering. The water bucket 222 further comprises a first water exit 228, for example, configured on the bottom of the water bucket 222 and coupled to the first water entrance 220 of the electrolysis tank 210 through a pipe, which can direct the pure water 224 in the water bucket 222 into the electrolysis tank 210 to fill up the electrolysis tank 210. The water bucket is better configured higher than the electrolysis tank 210 (as shown in FIG. 2, the bottom of the water bucket 222 is higher than the top of the electrolysis tank 210, or the bottom of the water bucket 222 only needs to be higher than the bottom of the electrolysis tank 210, for example, the bottom of the water bucket 222 is higher than a quarter from the bottom of the electrolysis tank 210). Therefore, the present invention can automatically fill up the electrolysis tank 210 through siphon pipes theory or gravity principle without other pressurized devices. Additionally, a pressure will be generated on the surface of the pure water 224 in the water bucket 222 because the gas mixture including hydrogen and oxygen 216 is guided into the water bucket 222, wherein the pressure can cause the water bucket 222 to automatically fill up the electrolysis tank 210.

The gas mixture including hydrogen and oxygen 216 which is cooled and filtered by the pure water 224 will be stored on the top of the bucket 222 and then output through the second gas exit 230 on the top for a user to breathe directly or for performing the follow-up atomized gas mixing process, which will be explained later. At the time, the output rate of the gas mixture including hydrogen and oxygen 216 can be within 0.1 L/min to 2 L/min. A pressure sensor 236 can be selectively configured on the top of the water bucket 222. A depressurize device 232, such as a depressurize valve, can be configured on the top of the water bucket 222. When the pressure of the gas mixture including hydrogen and oxygen 216 stored on the top of the water bucket 222 is high over a predetermined pressure, the water bucket 222 can be depressurized through the depressurize device 232. Therefore, hydrogen explosion can be prevented. That is to say, the water bucket 222 can be selectively depressurized by the depressurize device. For example, when the second gas exit 230 cannot output normally, such as blockage, the volume of hydrogen and oxygen in the first water bucket 222 will increase and then the pressure will increase as well because the electrolysis tank 210 is continuously generating the gas mixture including hydrogen and oxygen 216. The water bucket 222 can be depressurized through the depressurize device 232, which can prevent hydrogen explosion. In an embodiment, when the pressure is one Pascal, the depressurize process is set to be performed. The water bucket 222 further comprises a water level sensor 234, used to sense the water level of the pure water in the water bucket 222. The working method will be explained later.

If the water level sensor 234 senses the water level of the pure water 224 in the water bucket 222 is lower than a preset value, such as low water level 240, the water bucket 222 can be filled up through water filling entrance 244. The water level sensor 234 had better be connected to an alarm device, such as display device 108 shown in FIG. 1, which can display an alarm message or make alarm sound for reminding the user to fill up. The generated volume of the gas mixture including hydrogen and oxygen 216 is increased and the volume of the gas mixture including hydrogen and oxygen 216 stored on the top of the water bucket 222 is increased as well when the water bucket 222 continuously fills up the electrolysis tank 210 with pure water 224. As the result, the water level of the pure water 224 in the water bucket 222 becomes lower. Hydrogen explosion will probably happen if the volume of the gas mixture including hydrogen and oxygen 216 is too big. Therefore, the volume of the gas mixture including hydrogen and oxygen 216 in the water bucket 222 can be controlled through water level sensing function of the water level sensor 234. Through the depressurize process and the filling-up process mentioned above, the stored volume and pressure of the gas mixture including hydrogen and oxygen 216 in the water bucket 222 can be effectively controlled, which can prevent hydrogen explosion effectively. In some embodiments, the water level sensor 234 can be electrically connected to the power supply 260. When the water level of the water bucket 222 is sensed to be brought low continuously, and if the water level is lower than a preset value and there doesn't have fill up process, the power supply 260 can be cut off directly to stop electrolyzing and generating the gas mixture including hydrogen and oxygen 216 from the electrolysis tank 210, which can prevent hydrogen explosion due to the big volume of the gas mixture including hydrogen and oxygen 216 for enhancing the security of the system. When the water level sensor 234 senses the water level of the pure water 224 in the water bucket 222 is higher than a preset value, such as high water level 242, the process of filling up is stopped. In some embodiments, the present invention can remind the user to stop filling up through the alarm device mentioned above.

When the electrolysis tank is electrolyzing water, the electrolysis tank can not only generate gas mixture including hydrogen and oxygen through electrical energy but also raise the temperature of the electrolysis tank through the generated heat probably; after the cooling process for cooling the gas mixture including hydrogen and oxygen 216 by the pure water 224, the temperature of the water bucket 222 may be caused to raise; during the process of the power supply 260 supplying power to the electrolysis tank, the temperature of the power supply 260 may be caused to raise. For enhancing the security of the gas generator, a first temperature sensor 246 can be configured in the electrolysis tank 210, and/or a second temperature sensor 238 can be configured in the water bucket 222, and/or a third temperature sensor 262 (for example, on the circuit board) can be configured in the power supply 260, which is used to sense the temperature of the electrolysis tank 210, water bucket 222, and power supply 260. When the first temperature sensor 246, the second temperature sensor 238, and the third temperature sensor 262 sense the temperatures which are higher than each preset value, the alarm message can be displayed or the alarm sounds can be made through the alarm device mentioned above, such as display device 108. Additionally, the first temperature sensor 246, the second temperature sensor 238, and the third temperature sensor 262 had better electrically connected to the power supply 260. When the first temperature sensor 246, the second temperature sensor 238, and the third temperature sensor 262 sense the temperatures which are higher than each preset value, it means the system is abnormal, each of the first temperature sensor 246, the second temperature sensor 238, and the third temperature sensor 262 can cut off the power supply 260 and stop generating the gas mixture including hydrogen and oxygen for enhancing the security of the system. That is to say, the first temperature sensor 246, the second temperature sensor 238, and the third temperature sensor 262 can selectively cut off the power supply 260 and stop generating the gas mixture including hydrogen and oxygen.

For maintaining and cleaning conveniently, a first outlet 248 is configured in the electrolysis tank 210 and a second outlet 250 is configured in the water bucket 222. A first drain valve 254 can control the first outlet 248 to be open or close and a second drain valve 256 can control the second outlet 250 to be open or close. The first drain valve 254 and the second drain valve 256 can drain water for user to maintain or fix the electrolysis tank.

Figure 3:
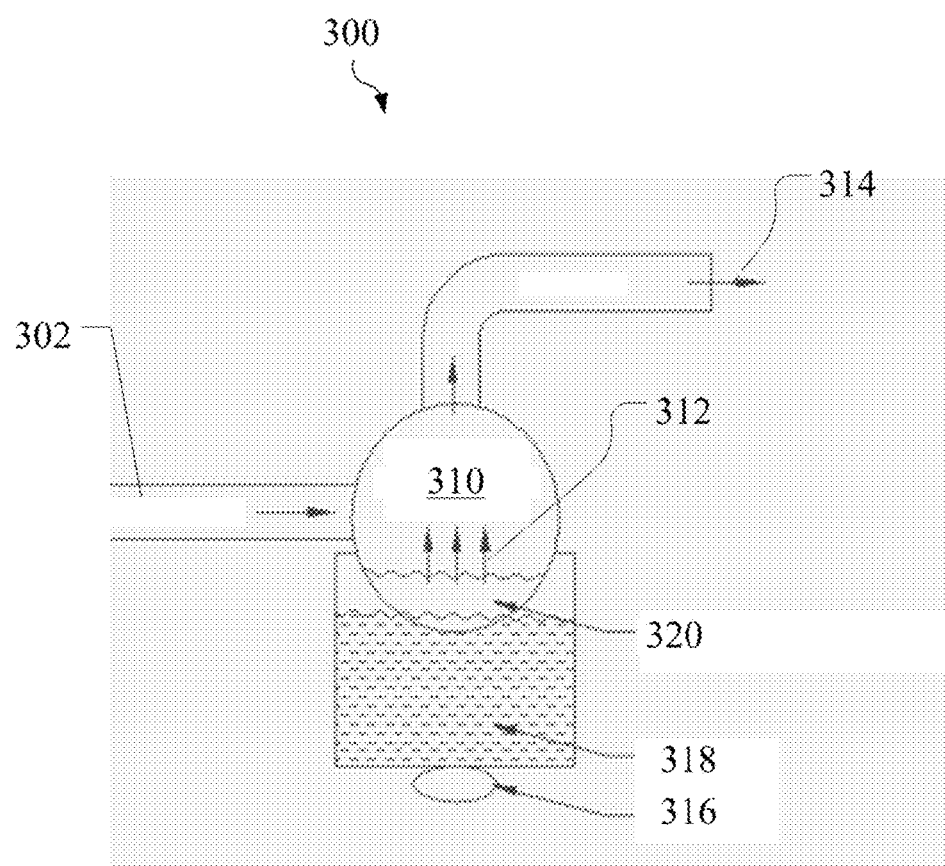
FIG. 3 shows the gas mixing system of the gas generator for health use in another embodiment of the present invention.

Please refer to FIG. 3. FIG. 3 shows the gas mixing system of the gas generator for health use in another embodiment of the present invention. The gas mixing system 300 is coupled to the second gas exit 230 of the water bucket 222 shown in FIG. 2, for example, coupled to the second gas exit 230 in FIG. 2 through pipe 302, for receiving gas mixture including hydrogen and oxygen 216. The gas mixing system 300 comprises an atomized/volatile gas mixing tank 310, used to mix the gas mixture including hydrogen and oxygen and an atomized/volatile gas 312 for generating health gas 314, and coupled to the pipe 104 shown in FIG. 1 for user to breathe. The atomized/volatile gas mixing tank 310 further comprises an oscillator 316, adapted to atomize or volatilize a liquid 318 and the liquid 320 in the atomized/volatile gas mixing tank 310 for generating the atomized/volatile gas 312. Liquid 318 is a base liquid of the oscillator 316, such as pure water. The liquid 320 is selected from a group consisting of an essential oil, a medicinal liquid, pure water and a combination thereof. The atomized/volatile gas 312 thus produced is preferably a volatile essential oil, an atomized medicinal liquid, atomized water vapor or a combination of two or three of above-mentioned volatile/atomized items. In some embodiments, the composition of the health gas can be selected by user. For example, the user can turn on/off the oscillator 316 to select the composition of the health gas. To elaborate, when the oscillator 316 is turned on, the health gas 314 is generated by mixing the atomized/volatile gas 312 and the gas mixture including hydrogen and oxygen. When the oscillator 316 is turned off, no atomized/volatile gas is generated and, in this case, the health gas 314 comprises only the gas mixture including hydrogen and oxygen. According to the statement mentioned above, the output device 110 of the gas generator 100 can be used to adjust the voltage of the oscillator 316 by user for controlling the spray of volatile essential oil, atomized medicinal liquid, or atomized water vapor and then mixing with the gas mixture including hydrogen and oxygen 216 mentioned above.

Figure 4:
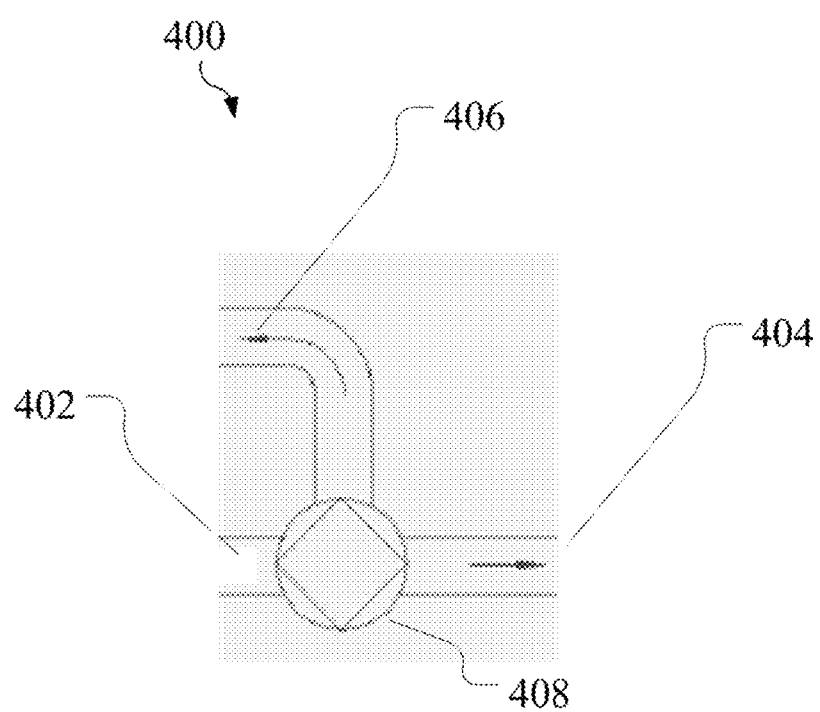
FIG. 4 shows the diversion device of the gas generator for health use in another embodiment of the present invention.

For enhancing the convenience when using, the gas generator 100 can further comprise a diversion device 400 (as FIG. 4), wherein the input pipe 402 of the diversion device 400 can be coupled to the second gas exit 230 of the water bucket 222. The diversion device 400 comprises a select switch 408, which can be controlled by the input device 110 of the gas generator 100 for outputting the gas mixture including hydrogen and oxygen 216 of the second gas exit 230 of the water bucket 222 through first supply pipe 404, through second supply pipe 406, or through both first supply pipe 404 and second supply pipe 406 concurrently. Therefore, the gas generator 100 can selectively supply for two users to use concurrently. When the gas generator 100 comprises gas mixing system 300, the input pipe 402 of the diversion device 400 can be used to receive health gas 314. And through the input device 110, the select switch 408 can be controlled for outputting the health gas 314 through first supply pipe 404, through second supply pipe 406, or through both first supply pipe 404 and second supply pipe 406 concurrently. Therefore, the gas generator 100 can selectively supply for two users to use concurrently.

Please refer to FIG. 1 again. In some embodiments, a gas leakage sensor 120 can be configured in the main body 102 of the gas generator 100 and electrically connected to the power supply 260 shown in FIG. 2. When the gas leakage sensor senses an abnormal gas leakage from the gas generator, which comprises the gas mixture generate device shown in FIG. 2 or gas mixing system shown in FIG. 3, the present invention cuts off the power supply 260 and displays an alarm message on the alarm device mentioned above. Additionally, an emergency button 112 can be configured in the main body 102 of the gas generator 100, electrically connected to the power supply 260 shown in FIG. 2. When the user meets an accidental situation, such as feeling uncomfortable, or an emergent change of the surrounding conditions, the user can press the emergency button 112 directly and the system will cut off the power supply 260. Upon the emergent situation is solved, the user can restart the gas generator 100.

According to the security system provided by the present invention, through the temperature configured in the electrolysis tank, water bucket, and power supply, the temperature of relative device can be monitored for preventing an air blast or a short circuit due to high temperature to enhance the security of the gas generator. Through the water level sensor configured in the water bucket, the water level of the water bucket can be monitored for controlling the filling water mechanism and the volume of the gas mixture including hydrogen and oxygen stored in the water bucket to prevent hydrogen explosion caused by high pressure or big volume of the gas mixture including hydrogen and oxygen stored in the water bucket. Therefore, the security of the gas generator can be insured. The gas leakage sensor can monitor if the gas generator has abnormal condition and turn off the system to avoid leakage of gas mixture including hydrogen and oxygen and prevent hydrogen explosion. The emergency button can turn off the system according to the emergent situation. According to the present invention, the gas generator can provide a safer using circumstance.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

The invention claimed is:

1. A gas generator for health use, comprising:
a power supply;
an electrolysis tank coupled to the power supply for containing electrolyzed water and electrolyzing the electrolyzed water to generate a gas mixture including hydrogen;
a water bucket containing supplemental electrolyzed water, wherein the electrolysis tank outputs the gas mixture including hydrogen to the water bucket, and the water bucket supplements the supplemental electrolyzed water to the electrolysis tank;
a gas mixing tank configured to generate a volatile essential oil, an atomized medicinal liquid, an atomized water vapor, or a combination thereof without the help of the gas mixture including hydrogen, the gas mixing tank receiving the gas mixture including hydrogen and mixing the gas mixture with the volatile essential oil, the atomized medicinal liquid, the atomized water vapor, or the combination thereof to generate a health gas, wherein the gas mixing tank further comprises an oscillator for atomizing or vaporizing a liquid to produce the volatile essential oil, the atomized medicinal liquid, the atomized water vapor, or the combination thereof, and the gas mixing tank is configured to selectively output the gas mixture including hydrogen or the health gas by turning on or turning off the oscillator; and
a temperature sensor coupled to a case of the electrolysis tank for sensing the temperature of the electrolysis tank to selectively cut off the electrolysis tank;
wherein the gas generator further comprises a water level sensor coupled to the case of the water bucket and configured to sense a water level of the water bucket, and the water level sensor is further configured to selectively control a filling up process of the electrolyzed water from water bucket to the electrolysis tank and reduce the stored volume of the gas mixture in the electrolysis tank, and the filling up process is stopped when the water level sensor senses the water level of the electrolyzed water in the water bucket higher than a preset value;
wherein the gas generator further comprises an input device configured to selectively adjust an output rate of the gas mixture including hydrogen of the gas generator at least including 2 liters per minute;
wherein the water bucket further comprises a gas inlet configured to input the gas mixture including hydrogen into the supplemental electrolyzed water in the water bucket.

2. The gas generator for health use of claim 1, wherein the gas generator further comprises a second temperature sensor coupled to the case of the water bucket for sensing the temperature of the water bucket to selectively cut off the power supply.

3. The gas generator for health use of claim 2, wherein the gas generator further comprises a third temperature sensor coupled to the power supply for sensing the temperature of the power supply to selectively cut off the power supply.

4. The gas generator for health use of claim 1, wherein the gas generator further comprises a gas leakage sensor coupled to the gas generator for sensing whether there is an abnormal gas leakage from the gas generator to selectively cut off the power supply.

5. The gas generator for health use of claim 1, wherein the gas generator further comprises an emergency button coupled to the power supply to selectively cut off the power supply by a user.

6. The gas generator for health use of claim 1, wherein the gas generator further comprises a displayer configured to display an operation condition of the gas generator.

7. The gas generator for health use of claim 1, wherein the gas generator further comprises a touch panel configured to selectively adjust an output rate of the volatile essential oil, the atomized medicinal liquid, the atomized water vapor, or the combination thereof.

8. A gas generator for health use, comprising:
   a power supply;
   an electrolysis tank containing electrolyzed water and coupled to the power supply for electrolyzing the electrolyzed water to generate a gas mixture including hydrogen;
   a water bucket containing supplemental electrolyzed water, wherein the electrolysis tank outputs the gas mixture including hydrogen to the water bucket, and the water bucket supplements the supplemental electrolyzed water to the electrolysis tank;
   a sensor to selectively control the power supply, wherein the sensor is selected from a group consisting of a water level sensor coupled to a case of the water bucket, a gas leakage sensor coupled to the gas generator, a temperature sensor coupled to the water bucket, a temperature sensor coupled to the electrolysis tank, a temperature sensor coupled to the power supply, and a combination thereof;
   a gas mixing tank comprising an oscillator for atomizing or vaporizing a liquid to produce a volatile essential oil, an atomized medicinal liquid, an atomized water vapor, or a combination thereof, and the gas mixing tank receiving the gas mixture including hydrogen and mixing the gas mixture with the volatile essential oil, the atomized medicinal liquid, the atomized water vapor, or the combination thereof to generate a health gas, wherein the gas mixing tank is configured to selectively output the gas mixture including hydrogen or the health gas by turning on or turning off the oscillator;
   a touch panel configured to display an operation condition of the gas generator, and a usage information of the gas generator by a user, and configured to selectively adjust an output rate of the gas mixture including hydrogen of the gas generator; and
   a network system configured to transfer the operation condition of the gas generator or the usage information of the gas generator by the user to an external database, and configured to provide updating function to the gas generator;
   wherein the water bucket further comprises a gas inlet configured to input the gas mixture including hydrogen into the supplemental electrolyzed water in the water bucket.

9. The gas generator for health use of claim 8, wherein the touch panel is configured to generate an alarm message when the sensor cuts off the power supply.

* * * * *